US009365470B2

(12) United States Patent
Leflaive et al.

(10) Patent No.: US 9,365,470 B2
(45) Date of Patent: Jun. 14, 2016

(54) SIMULATED COUNTERCURRENT CHROMATOGRAPHIC SEPARATION PROCESS AND DEVICE WITH LOW PRESSURE DROP AND HIGH NUMBER OF ZONES

(75) Inventors: Philibert Leflaive, Mions (FR); Damien Leinekugel Le Cocq, Lyons (FR)

(73) Assignee: IFP Energies Nouvelles, Rueil-Malmaison (FR)

( * ) Notice: Subject to any disclaimer, the term of this patent is extended or adjusted under 35 U.S.C. 154(b) by 346 days.

(21) Appl. No.: 14/125,317

(22) PCT Filed: Apr. 26, 2012

(86) PCT No.: PCT/FR2012/000161
§ 371 (c)(1),
(2), (4) Date: Feb. 12, 2014

(87) PCT Pub. No.: WO2012/172190
PCT Pub. Date: Dec. 20, 2012

(65) Prior Publication Data
US 2014/0148633 A1 May 29, 2014

(30) Foreign Application Priority Data

Jun. 16, 2011 (FR) ...................................... 11 01854

(51) Int. Cl.
*C07C 7/12* (2006.01)
*C07C 7/13* (2006.01)
*B01D 15/18* (2006.01)

(52) U.S. Cl.
CPC .............. *C07C 7/12* (2013.01); *B01D 15/1807* (2013.01); *B01D 15/1842* (2013.01); *C07C 7/13* (2013.01)

(58) Field of Classification Search
None
See application file for complete search history.

(56) References Cited

U.S. PATENT DOCUMENTS

| 5,882,523 A | 3/1999 | Hotier et al. |
| 6,017,448 A | 1/2000 | Hotier et al. |
| 7,582,208 B2 | 9/2009 | Hotier et al. |
| 2008/0237132 A1 | 10/2008 | Hotier et al. |

FOREIGN PATENT DOCUMENTS

| EP | 0821988 A1 | 2/1998 |
| FR | 2913345 A1 | 9/2008 |

OTHER PUBLICATIONS

International Search Report and Written Opinion from PCT/FR2012/000161 dated Jul. 5, 2012.
Alexandre Nicolaos et al. "Application of Equilibrium Theory to Ternary Moving Bed Configurations (four+four, five+four, eight and nine zones) I. Linear case" Journal of Chromatography A., vol. 908, No. 1-2, [2001], pp. 71-86.

*Primary Examiner* — Tam M Nguyen
(74) *Attorney, Agent, or Firm* — Millen, White, Zelano & Branigan, P.C.

(57) ABSTRACT

A simulated moving bed separation process is characterized in that the feed and desorbant injection streams are each divided into N streams (N being a whole number strictly greater than 1) injected respectively at N distinct feed injection points and at N distinct desorbant injection points, and in that the extract and raffinate withdrawal points are also each divided into N streams each withdrawn from N distinct withdrawal points, the device being constituted by 4×N chromatographic zones.

8 Claims, 3 Drawing Sheets

(Invention)

(invention)

(invention)

SIMULATED COUNTERCURRENT CHROMATOGRAPHIC SEPARATION PROCESS AND DEVICE WITH LOW PRESSURE DROP AND HIGH NUMBER OF ZONES

FIELD OF THE INVENTION

The invention relates to the field of separations of natural or chemical products which are difficult to separate by distillation. A family of processes and associated devices which are known as simulated moving bed or simulated counter-current processes are used; we shall hereinafter designate them generally as "SCC" processes.

A non-exhaustive list of fields which employ this type of processes includes:
  separation of normal paraffins from branched paraffins, naphthenes and aromatics;
  olefin/paraffin separation;
  separation of para-xylene from other aromatic C8 isomers;
  separation of meta-xylene from other aromatic C8 isomers;
  separation of ethylbenzene from other aromatic C8 isomers.

Beyond refineries and petrochemicals plants, there are many other applications that can be cited, including glucose/fructose separation, and the separation of positional isomers of cresol, optical isomers, etc.

PRIOR ART

SCC separation processes are well known in the art. As a general rule, an adsorber operating in simulated counter-current mode comprises at least three zones, and possibly four or five, each of those zones being constituted by a certain number of successive beds and each zone being defined by its position between a supply point and a withdrawal point. Typically, a SCC column is supplied with at least one feed F to be fractionated and a desorbant D (sometimes termed the eluent); at least one raffinate R and an extract E are withdrawn from said column.

The supply and withdrawal points are modified with time, i.e. shifted in the same direction by a value corresponding to one bed. Shifting the various injection or withdrawal points may be carried out either simultaneously or non-simultaneously, as disclosed in the patent U.S. Pat. No. 6,136,198. The process in the second variation is termed the VARICOL process.

Conventionally, 4 different chromatographic zones are defined in a SCC unit:
  zone 1: zone for desorption of compounds of the extract, included between the injection of desorbant D and the removal of extract E;
  zone 2: zone for desorption of compounds of the raffinate, included between the removal of extract E and the injection of feed to be fractionated F;
  zone 3: zone for adsorption of compounds of the extract, included between the injection of the feed and the withdrawal of raffinate R;
  zone 4: zone included between the withdrawal of raffinate and the injection of desorbant.

The prior art describes various devices and processes for carrying out the separation of feeds using simulated counter-current in great detail.

Particular patents that may be cited are U.S. Pat. Nos. 2,985,589, 3,214,247, 3,268,605, 3,592,612, 4,614,204, 4,378,292, 5,200,075 and U.S. Pat. No. 5,316,821.

Pressure drops in SCC processes are directly linked to interstitial velocities of the fluid phase in the chromatographic columns. The term "interstitial velocity" means the actual velocity of the fluid between the particles constituting the solid adsorbent.

Pressure drops play a major role in dimensioning the recirculating pump or pumps, the thickness of the walls of the adsorbers, the size of the support systems of any distribution plates, the mechanical behaviour of the grains of adsorbent, etc. They may become the limiting factor in the implementation of a SCC process.

The present invention aims to provide a SCC type process with a reduced pressure drop compared with the prior art, with the particular aim of reducing mechanical stresses in the various adsorbers or chromatographic columns by increasing the number of chromatographic zones, while keeping performance (purity, yield and productivity) very high.

The process of the invention can be used to achieve a productivity that is higher than that which would be obtained with a prior art SCC process with a large number of beds (more than 8 beds) and for which a maximum flow rate of treated feed is imposed by the pressure drops or the maximum admissible interstitial velocity in the unit.

DESCRIPTION OF THE INVENTION

Figure 1:
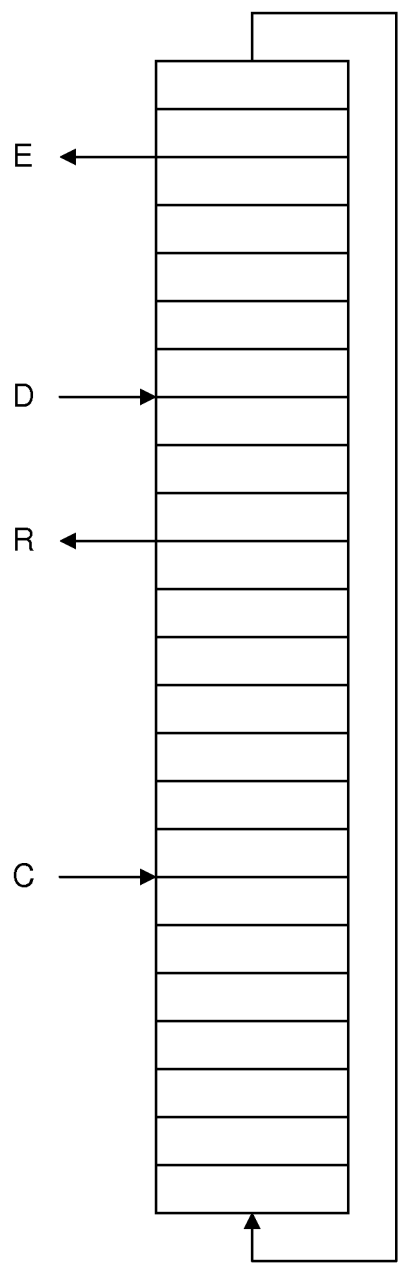
FIG. 1 represents a prior art SCC device constituted by 24 beds distributed into 4 zones.
Figure 2:
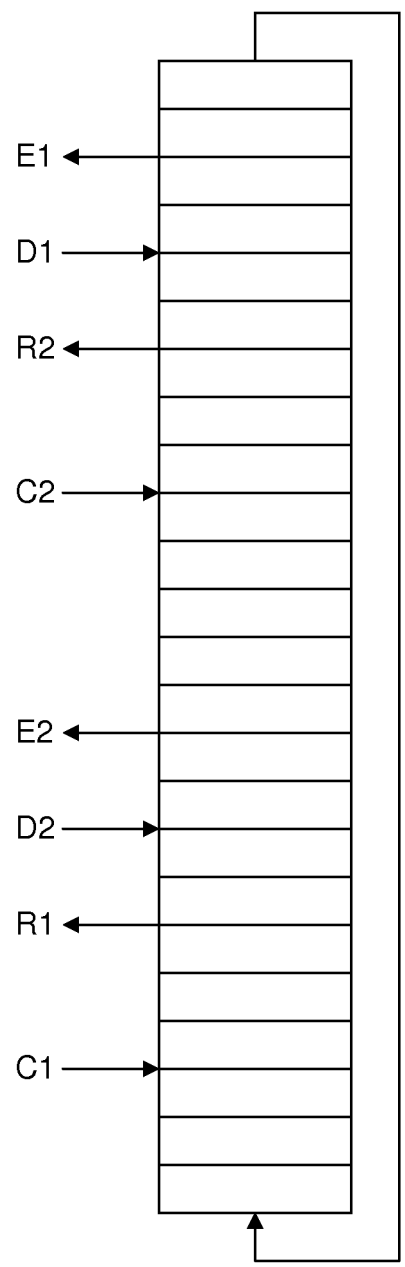
FIG. 2 represents a device of the invention, constituted by 24 beds distributed into 8 zones.
Figure 3:
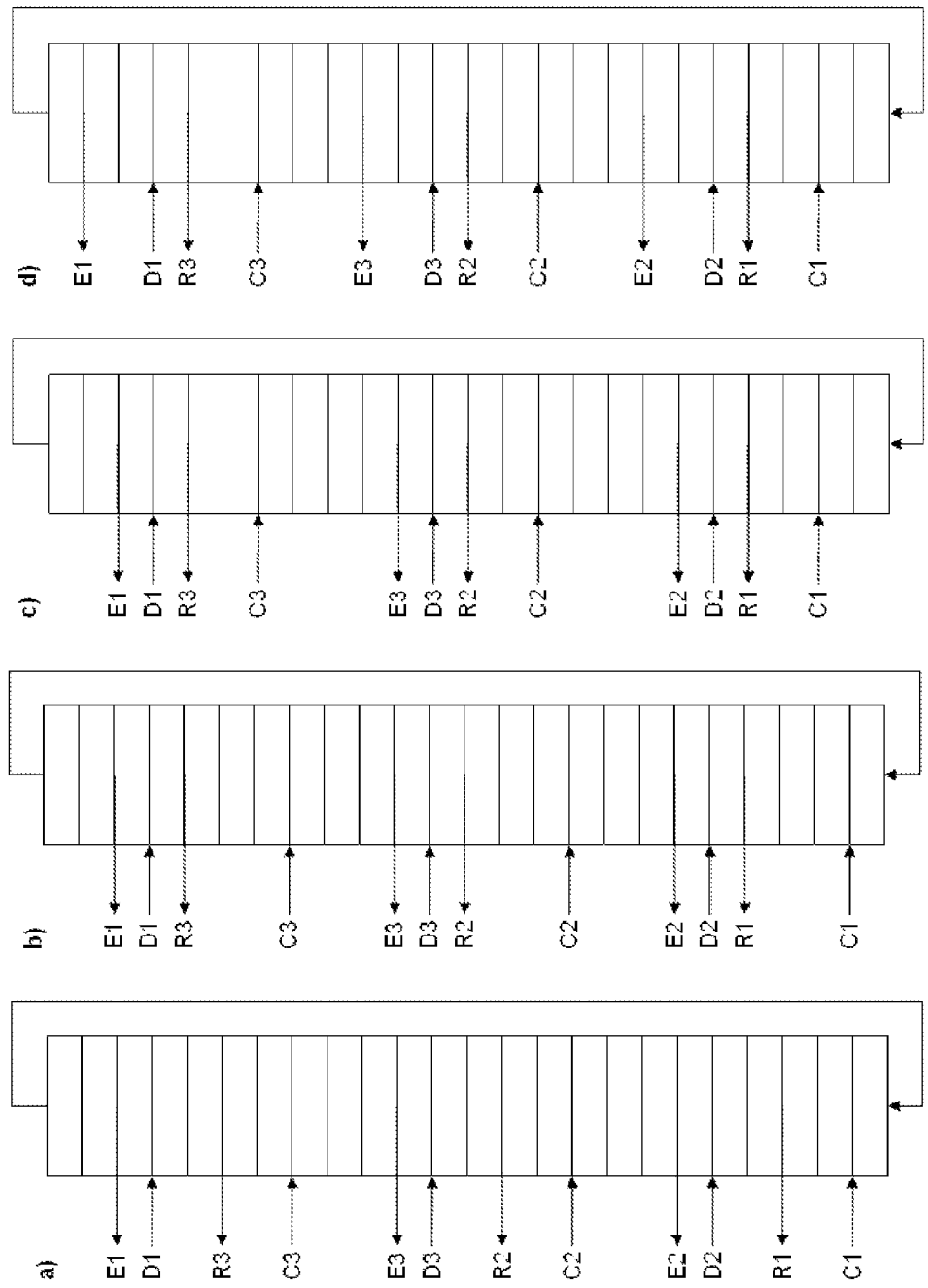
FIG. 3 represents a device of the invention, constituted by 24 beds distributed into 12 zones.

The present invention concerns a process for separation, by simulated counter-current chromatography (abbreviated to SCC), of a feed F, characterized in that the feed and desorbant injection streams are each divided into N streams (N being a whole number strictly greater than 1), injected respectively into N distinct feed injection points and N distinct desorbant injection points, and in that the extract and raffinate withdrawal streams are also each divided into N streams each withdrawn from N distinct withdrawal points, the device being constituted by 4×N chromatographic zones.

The injection and withdrawal points are positioned such that:
  a desorbant injection point is positioned between the raffinate withdrawal point and an extract withdrawal point, the 3 raffinate withdrawal, desorbant injection and extract withdrawal points being consecutive;
  an extract withdrawal point is positioned between a desorbant injection point and a feed injection point, the 3 desorbant injection, extract withdrawal and feed injection points being consecutive;
  a feed injection point is positioned between an extract withdrawal point and a raffinate withdrawal point, the 3 extract withdrawal, feed injection and raffinate withdrawal points being consecutive;
  a raffinate withdrawal point is positioned between a feed injection point and a desorbant injection point, the 3 feed injection, raffinate withdrawal and desorbant injection points being consecutive.

The term "consecutive" means that no other withdrawal or injection point is present between the points designated as consecutive.

It will also be noted that the three consecutive points always follow each other in the order injection, withdrawal, injection or on the order withdrawal, injection, withdrawal.

Compared with a process with the same geometry, treating the same feed flow and constituted by 4 zones, the process of the invention has a substantially reduced overall pressure drop and substantially equivalent performance.

The period at which the injection and withdrawal points is switched is multiplied by N in the process of the invention compared with a process with the same geometry, treating the same feed flow and constituted by 4 zones. The period at which the injection and withdrawal points is switched is defined as the time between two successive switches of the same injection or withdrawal stream.

The process of the present invention is of particular application to the separation of para-xylene or meta-xylene in a mixture of aromatic C8 hydrocarbons.

Clearly, these two application examples are in no way limiting and other applications are possible, in particular in the field of separation of normal- and iso-paraffins or normal- and iso-olefins.

The process for simulated counter-current (SCC) chromatographic separation of a feed F of the present invention has a number N of feed and desorbant injection points and extract and raffinate withdrawal points in the range 2 to 6, preferably in the range 2 to 4.

The process for simulated counter-current (SCC) chromatographic separation of a feed F of the present invention has a total number of beds of 16, 24 or 30. Preferably, the total number of beds is 24.

In a variation of the process for simulated counter-current (SCC) chromatographic separation of a feed F of the present invention, the number of beds in each of the zones varies by one bed during a switch period, the switch period of the injection and withdrawal points being defined as the time between two successive switches of the same injection or withdrawal stream.

Preferably, streams of the same type, i.e. the set of feed supply streams, the set of desorbant supply streams, the set of extract withdrawal streams and the set of raffinate withdrawal streams, have the same flow rate plus or minus 10%.

The remainder of the description of the process of the invention pertains to the particular case in which N=2, i.e. when:
  each feed injection point is divided into two, denoted F1 and F2;
  each desorbant injection point is divided into two, denoted D1 and D2;
  each extract withdrawal point is divided into two, denoted E1 and E2;
  each raffinate withdrawal point is divided into two, denoted R1 and R2.

The particular case in which N=2 corresponds to a SCC process with 8 zones defined as follows:
  zone 1 between desorbant injection No. 1 D1 and extract withdrawal No. 1 E1;
  zone 2 between extract withdrawal No. 1 E1 and feed injection No. 1 F1;
  zone 3 between feed injection No. 1 F1 and raffinate withdrawal No. 1 R1;
  zone 4 between raffinate withdrawal No. 1 R1 and desorbant injection No. 2 D2;
  zone 5 between desorbant injection No. 2 D2 and extract withdrawal No. 2 E2;
  zone 6 between extract withdrawal No. 2 E2 and feed injection No. 2 F2;
  zone 7 between feed injection No. 2 F2 and raffinate withdrawal No. 2 R2;
  zone 8 between raffinate withdrawal No. 2 R2 and desorbant injection No. 1 D1.

In the particular case in which N=3, i.e. in the case of a SCC process having 12 zones, the zones are defined as follows:
  zone 1 between desorbant injection No. 1 D1 and extract withdrawal No. 1 E1;
  zone 2 between extract withdrawal No. 1 E1 and feed injection No. 1 F1;
  zone 3 between feed injection No. 1 F1 and raffinate withdrawal No. 1 R1;
  zone 4 between raffinate withdrawal No. 1 R1 and desorbant injection No. 2 D2;
  zone 5 between desorbant injection No. 2 D2 and extract withdrawal No. 2 E2;
  zone 6 between extract withdrawal No. 2 E2 and feed injection No. 2 F2;
  zone 7 between feed injection No. 2 F2 and raffinate withdrawal No. 2 R2;
  zone 8 between raffinate withdrawal No. 2 R2 and desorbant injection No. 3 D3;
  zone 9 between desorbant injection No. 3 D3 and extract withdrawal No. 3 E3;
  zone 10 between extract withdrawal No. 3 E1 and feed injection No. 3 F3;
  zone 11 between feed injection No. 3 F1 and raffinate withdrawal No. 3 R3;
  zone 12 between raffinate withdrawal No. 3 R3 and desorbant injection No. D1.

These divisions into 8 and 12 zones will be better understood from the examples below.

The process for simulated counter-current chromatographic (SCC) separation of a feed F of the present invention may have a variation in which the number of beds in each of the zones varies from one bed during a switch period, the switch period of the injection and withdrawal points being defined as the time between two successive switches of the same injection or withdrawal stream.

Of the various applications of the process of the present invention that can be cited, the separation of para-xylene from a mixture of aromatic C8 hydrocarbons is particularly suitable. The separation of meta-xylene from a mixture of aromatic C8 hydrocarbons can also be cited.

EXAMPLES

The invention will be better understood from the following three examples.

Example 1 (In Accordance With The Prior Art)

A SCC unit was considered, constituted by 24 beds with a length of 1.1 m and an internal radius of 3.5 m, with feed injection, desorbant injection, extract withdrawal and raffinate withdrawal.

The shifts of the various injection or withdrawal points were simultaneous. The beds were distributed into 4 chromatographic zones in accordance with the configuration:

5/9/7/3 i.e. the distribution of the beds was as follows:
  5 beds in zone 1 (between the desorbant injection D and the extract withdrawal E);
  9 beds in zone 2 (between the extract withdrawal E and the feed injection F);

7 beds in zone 3 (between the feed injection F and the raffinate withdrawal R);

3 beds in zone 4 (between the raffinate withdrawal R and the desorbant injection D).

The adsorbent used was a BaX type zeolite and the desorbant was para-diethylbenzene. The temperature was 175° C. and the pressure was 15 bars.

The feed was composed of 20% para-xylene, 24% ortho-xylene, 51% meta-xylene and 5% ethylbenzene. The switch period employed was 70.8 seconds.

The feed and desorbant injection flow rates were as follows:

6.81 m$^3$/min for the feed;

7.48 m$^3$/min for the desorbant.

In addition, the flow rate in zone 4 was 22.08 m$^3$/min and the extract withdrawal flow rate was 4.38 m$^3$/min.

On simulation, a purity of 99.85% was obtained for the para-xylene, with a para-xylene yield of 97.39%.

The pressure drops over the whole of the adsorber constituted by 24 beds and 25 plates was 6.4 bar.

Example 2 (In Accordance With The Invention)

A unit in accordance with the invention was considered, constituted by 24 beds with a length of 1.1 m and an internal radius of 3.5 m, with two feed injections, two desorbant injections, two extract withdrawals and two raffinate withdrawals.

The shifts of the various injection or withdrawal points were simultaneous.

The beds were distributed into 8 chromatographic zones in accordance with the configuration:

2/5/3/2/2/5/3/2 i.e. the distribution of the beds was as follows:

2 beds in zone 1 (between the desorbant injection No. 1 D1 and the extract withdrawal No. E1);

5 beds in zone 2 (between the extract withdrawal No. 1 E1 and the feed injection No. 1 F1);

3 beds in zone 3 (between the feed injection No. 1 F1 and the raffinate withdrawal No. 1 R1);

2 beds in zone 4 (between the raffinate withdrawal No. 1 R1 and the desorbant injection No. 2 D2);

2 beds in zone 5 (between the desorbant injection No. 2 D2 and the extract withdrawal No. 2 E2);

5 beds in zone 6 (between the extract withdrawal No. 2 E2 and the feed injection No. 2 F2);

3 beds in zone 7 (between the feed injection No. 2 F2 and the raffinate withdrawal No. 2 R2);

2 beds in zone 8 (between the raffinate withdrawal No. 2 R2 and the desorbant injection No. 1 D1).

The adsorbent used was a BaX type zeolite and the desorbant was para-diethylbenzene. The temperature was 175° C. and the pressure was 15 bars.

The feed was composed of 20% para-xylene, 24% ortho-xylene, 51% meta-xylene and 5% ethylbenzene. The switch period employed was 141.6 seconds.

The feed and desorbant injection flow rates were as follows:

3.405 m$^3$/min for feed no 1;

3.405 m$^3$/min for feed no 2;

3.74 m$^3$/min for desorbant no 1;

3.74 m$^3$/min for desorbant no 2.

In addition, the flow rates in zone 4 and zone 8 were 11.08 m$^3$/min and the 2 extract withdrawal flow rates were 2.25 m$^3$/min.

On simulation, a purity of 99.86% was obtained for the para-xylene, with a para-xylene yield of 95.5%.

The pressure drops over the whole of the adsorber constituted by 24 beds and 25 plates was 2.5 bar.

Example 3 (In Accordance With The Invention)

A unit in accordance with the invention was considered, constituted by 24 beds with a length of 1.1 m and an internal radius of 3.5 m, with three feed injections, three desorbant injections, three extract withdrawals and three raffinate withdrawals.

The shifts of the various injection or withdrawal points were not simultaneous, so as to obtain non-integral chromatographic zone lengths (as disclosed in U.S. Pat. No. 6,136, 198).

The beds were distributed into 12 chromatographic zones in accordance with the configuration:

1.5/3.2/2.1/1.2/1.5/3.2/2.1/1.2/1.5/3.2/2.1/1.2 i.e. the distribution of the beds was as follows during a period (assuming that, by convention, the start and end of a period is defined by the shifting of the desorbant injection points):

from the start of the period to 42.6 seconds (defined with respect to the start of the period), there was/were:

1 bed in zone 1 (between the desorbant injection No. 1 D1 and the extract withdrawal No. E1);

3 beds in zone 2 (between the extract withdrawal No. 1 E1 and the feed injection No. 1 F1);

2 beds in zone 3 (between the feed injection No. 1 F1 and the raffinate withdrawal No. 1 R1);

2 beds in zone 4 (between the raffinate withdrawal No. 1 R1 and the desorbant injection No. 2 D2);

1 bed in zone 5 (between the desorbant injection No. 2 D2 and the extract withdrawal No. 2 E2);

3 beds in zone 6 (between the extract withdrawal No. 2 E2 and the feed injection No. 2 F2);

2 beds in zone 7 (between the feed injection No. 2 F2 and the raffinate withdrawal No. 2 R2);

2 beds in zone 8 (between the raffinate withdrawal No. 2 R2 and the desorbant injection No. 3 D3);

1 bed in zone 9 (between the desorbant injection No. 3 D3 and the extract withdrawal No. 3 E3);

3 beds in zone 10 (between the extract withdrawal No. 3 E3 and the feed injection No. 3 F3);

2 beds in zone 11 (between the feed injection No. 3 F3 and the raffinate withdrawal No. 3 R3);

2 beds in zone 12 (between the raffinate withdrawal No. 3 R3 and the desorbant injection No. 1 D1);

from 42.6 seconds to 63.9 seconds (defined with respect to the start of the period), there was/were:

1 bed in zone 1 (between the desorbant injection No. 1 D1 and the extract withdrawal No. E1);

3 beds in zone 2 (between the extract withdrawal No. 1 E1 and the feed injection No. 1 F1);

3 beds in zone 3 (between the feed injection No. 1 F1 and the raffinate withdrawal No. 1 R1);

1 bed in zone 4 (between the raffinate withdrawal No. 1 R1 and the desorbant injection No. 2 D2);

1 bed in zone 5 (between the desorbant injection No. 2 D2 and the extract withdrawal No. 2 E2);

3 beds in zone 6 (between the extract withdrawal No. 2 E2 and the feed injection No. 2 F2);

3 beds in zone 7 (between the feed injection No. 2 F2 and the raffinate withdrawal No. 2 R2);

1 bed in zone 8 (between the raffinate withdrawal No. 2 R2 and the desorbant injection No. 3 D3);

1 bed in zone 9 (between the desorbant injection No. 3 D3 and the extract withdrawal No. 3 E3);
3 beds in zone 10 (between the extract withdrawal No. 3 E3 and the feed injection No. 3 F3);
3 beds in zone 11 (between the feed injection No. 3 F3 and the raffinate withdrawal No. 3 R3);
1 bed in zone 12 (between the raffinate withdrawal No. 3 R3 and the desorbant injection No. 1 D1);

from 63.9 seconds to 106.5 seconds (defined with respect to the start of the period), there was/were:
1 bed in zone 1 (between the desorbant injection No. 1 D1 and the extract withdrawal No. E1);
4 beds in zone 2 (between the extract withdrawal No. 1 E1 and the feed injection No. 1 F1);
2 beds in zone 3 (between the feed injection No. 1 F1 and the raffinate withdrawal No. 1 R1);
1 bed in zone 4 (between the raffinate withdrawal No. 1 R1 and the desorbant injection No. 2 D2);
1 bed in zone 5 (between the desorbant injection No. 2 D2 and the extract withdrawal No. 2 E2);
4 beds in zone 6 (between the extract withdrawal No. 2 E2 and the feed injection No. 2 F2);
2 beds in zone 7 (between the feed injection No. 2 F2 and the raffinate withdrawal No. 2 R2);
1 bed in zone 8 (between the raffinate withdrawal No. 2 R2 and the desorbant injection No. 3 D3);
1 bed in zone 9 (between the desorbant injection No. 3 D3 and the extract withdrawal No. 3 E3);
4 beds in zone 10 (between the extract withdrawal No. 3 E3 and the feed injection No. 3 F3);
2 beds in zone 11 (between the feed injection No. 3 F3 and the raffinate withdrawal No. 3 R3);
1 bed in zone 12 (between the raffinate withdrawal No. 3 R3 and the desorbant injection No. 1 D1);

from 63.9 seconds (defined with respect to the start of the period to the end of the period, there was/were:
2 beds in zone 1 (between the desorbant injection No. 1 D1 and the extract withdrawal No. E1);
3 beds in zone 2 (between the extract withdrawal No. 1 E1 and the feed injection No. 1 F1);
2 beds in zone 3 (between the feed injection No. 1 F1 and the raffinate withdrawal No. 1 R1);
1 bed in zone 4 (between the raffinate withdrawal No. 1 R1 and the desorbant injection No. 2 D2);
2 beds in zone 5 (between the desorbant injection No. 2 D2 and the extract withdrawal No. 2 E2);
3 beds in zone 6 (between the extract withdrawal No. 2 E2 and the feed injection No. 2 F2);
2 beds in zone 7 (between the feed injection No. 2 F2 and the raffinate withdrawal No. 2 R2);
1 bed in zone 8 (between the raffinate withdrawal No. 2 R2 and the desorbant injection No. 3 D3);
2 beds in zone 9 (between the desorbant injection No. 3 D3 and the extract withdrawal No. 3 E3);
3 beds in zone 10 (between the extract withdrawal No. 3 E3 and the feed injection No. 3 F3);
2 beds in zone 11 (between the feed injection No. 3 F3 and the raffinate withdrawal No. 3 R3);
1 bed in zone 12 (between the raffinate withdrawal No. 3 R3 and the desorbant injection No. 1 D1).

The adsorbent used was a BaX type zeolite and the desorbant was para-diethylbenzene. The temperature was 175° C. and the pressure was 15 bars.

The feed was composed of 20% para-xylene, 24% ortho-xylene, 51% meta-xylene and 5% ethylbenzene. The switch period employed was 212.4 seconds.

The feed and desorbant injection flow rates were as follows:
2.27 m$^3$/min for feed no 1;
2.27 m$^3$/min for feed no 2;
2.27 m$^3$/min for feed no 3;
2.493 m$^3$/min for desorbant no 1;
2.493 m$^3$/min for desorbant no 2;
2.493 m$^3$/min for desorbant no 3.

In addition, the flow rates in zones 4, 8 and 12 were 7.36 m$^3$/min and the three extract withdrawal flow rates were 1.46 m$^3$/min.

On simulation, a purity of 99.82% was obtained for the para-xylene, with a para-xylene yield of 95.54%.

The pressure drops over the whole of the adsorber constituted by 24 beds and 25 plates was 1.5 bar.

The invention claimed is:

1. A process for simulated counter-current (SCC) chromatographic separation of a feed F having at least one adsorption column divided into zones, each zone comprising a certain number of beds, said column being composed of a plurality of beds of adsorbent separated by plates $P_i$ each comprising a distribution/extraction system, in which process the feed F is supplied to at least one supply point and a desorbant D is supplied to at least one supply point, and at least one extract E and at least one raffinate R are extracted, the supply and withdrawal points being shifted over time by a value corresponding to one bed of adsorbent with a switch period ST and determining a plurality of functional zones of the SMB, each zone being included between an injection point and the immediately consecutive withdrawal point, or between a withdrawal point and the immediately consecutive injection point;

the process being characterized in that the feed and desorbant injection streams are each divided into N streams (N being a whole number strictly greater than 1), injected respectively into N distinct feed injection points and N distinct desorbant injection points, and in that the extract and raffinate withdrawal streams are also each divided into N streams each withdrawn from N distinct withdrawal points, the device being constituted by 4×N chromatographic zones, in which process the injection and withdrawal points are positioned such that:

a desorbant injection point is positioned between the raffinate withdrawal point and an extract withdrawal point, the 3 points: raffinate withdrawal, desorbant injection and extract withdrawal, being consecutive;

an extract withdrawal point is positioned between a desorbant injection point and a feed injection point, the 3 points: desorbant injection, extract withdrawal and feed injection, being consecutive;

a feed injection point is positioned between an extract withdrawal point and a raffinate withdrawal point, the 3 points: extract withdrawal, feed injection and raffinate withdrawal, being consecutive;

a raffinate withdrawal point is positioned between a feed injection point and a desorbant injection point, the 3 points: feed injection, raffinate withdrawal and desorbant injection, being consecutive.

2. A process for simulated counter-current (SCC) chromatographic separation of a feed F according to claim 1, in which streams of the same type (feed, desorbant, extract or raffinate) have the same flow rate plus or minus 10%.

3. A process for simulated counter-current (SCC) chromatographic separation of a feed F according to claim 1, in which the number N of feed and desorbant injection points and extract and raffinate withdrawal points is in the range 2 to 6.

4. A process for simulated counter-current (SCC) chromatographic separation of a feed F according to claim 1, in which the total number of beds is 16, 24 or 30.

5. A process for simulated counter-current (SCC) chromatographic separation of a feed F according to claim 1, in which the number of beds in each of the zones varies by one bed during a switch period, the switch period of the injection and withdrawal points being defined as the time between two successive switches of the same injection or withdrawal stream.

6. Application of a simulated counter-current chromatographic process according to claim 1 to the separation of para-xylene from a mixture of aromatic C8 hydrocarbons.

7. Application of a simulated counter-current chromatographic process according to claim 1 to the separation of meta-xylene from a mixture of aromatic C8 hydrocarbons.

8. A process for simulated counter-current (SCC) chromatographic separation of a feed F according to claim 1, in which the number N of feed and desorbant injection points and extract and raffinate withdrawal points is in the range 2 to 4.

\* \* \* \* \*